United States Patent [19]

Bock et al.

[11] 4,177,342

[45] Dec. 4, 1979

[54] PROCESS FOR THE PREPARATION OF POLYISOCYANATES CONTAINING ALLOPHANATE GROUPS

[75] Inventors: Manfred Bock, Leverkusen; Josef Pedain; Wilhelm Slawyk, both of Cologne; Klaus König, Leverkusen, all of Fed. Rep. of Germany

[73] Assignee: Bayer Aktiengesellschaft, Leverkusen, Fed. Rep. of Germany

[21] Appl. No.: 909,239

[22] Filed: May 24, 1978

[30] Foreign Application Priority Data

Jun. 4, 1977 [DE] Fed. Rep. of Germany ....... 2725318

[51] Int. Cl.$^2$ ...................... C08G 18/32; C08G 18/79; C08G 18/80
[52] U.S. Cl. ......................................... 528/45; 427/30; 427/185; 528/44; 528/49; 528/59; 528/65; 528/85
[58] Field of Search ...................... 528/44, 45, 49, 85, 528/59, 65

[56] References Cited

U.S. PATENT DOCUMENTS

| | | | |
|---|---|---|---|
| 3,248,373 | 4/1966 | Baninger | 521/164 |
| 3,368,985 | 2/1968 | Wismer et al. | 521/164 |
| 3,397,184 | 8/1968 | Heydkamp et al. | 528/46 |
| 3,491,067 | 1/1970 | Sellet | 528/85 |
| 3,595,814 | 7/1971 | Lloyd et al. | 521/164 |
| 3,769,318 | 10/1973 | Windemuth et al. | 521/124 |
| 4,070,345 | 1/1978 | Winkelmann et al. | 528/65 |
| 4,107,151 | 8/1978 | Takahashi et al. | 528/65 |

FOREIGN PATENT DOCUMENTS

994890 6/1965 United Kingdom.

*Primary Examiner*—H. S. Cockeram
*Attorney, Agent, or Firm*—Gene Harsh; Lawrence S. Pope

[57] ABSTRACT

This invention relates to a new process for the preparation of new organic polyisocyanates having at least three isocyanate groups and containing allophanate groups, to the polyisocyanates obtainable by this process, and to their use as components for the production of polyurethane resins.

9 Claims, No Drawings

PROCESS FOR THE PREPARATION OF POLYISOCYANATES CONTAINING ALLOPHANATE GROUPS

BACKGROUND OF THE INVENTION

Organic polyisocyanates containing allophanate groups and having aliphatically-bound isocyanate groups have already been disclosed, for example in British Patent Specification No. 994,890. According to this Patent Specification, urethane polyisocyanates obtained from simple monohydric or polyhydric alcohols and organic polyisocyanates, in particular diisocyanates, are reacted with further quantities of organic polyisocyanates, preferably diisocyanates, by several hours heating at elevated temperatures or in the presence of catalysts, to form polyisocyanates which contain allophanate groups. A particular disadvantage of this process, apart from the use of catalysts, is that the allophanatization reaction is carried out under conditions of prolonged heating which generally leads to discolored reaction products.

A new process has now surprisingly been found which makes it possible for new organic polyisocyanates containing allophanate groups and having aliphatically or cycloaliphatically bound isocyanate groups to be obtained without the use of catalysts or prolonged heating comparable to that required in the process according to British Patent No. 994,890. The products obtained by the process according to the invention are, therefore, distinguished by their low tinting value and they also have a comparatively low viscosity. They are valuable starting materials for the production of polyurethane resins, particularly for the production of polyurethane lacquers.

SUMMARY OF THE INVENTION

The present invention relates to a process for the preparation of allophanate polyisocyanates having at least three isocyanate groups by the reaction of hydroxyl compounds with excess quantities of organic polyisocyanates which are free from allophanate groups, characterized in that the hydroxyl compounds used are compounds of the following formula

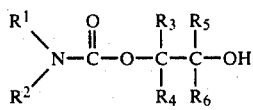

in which $R^1$ and $R^2$, which may be the same or different, represent hydrogen or hydroxy alkyl, alkyl or cycloalkyl groups but at least one of the groups $R^1$ and $R^2$ must be hydrogen or a hydroxy alkyl group, and $R_3$, $R_4$, $R_5$ and $R_6$, which may be the same or different, represent hydrogen or alkyl or hydroxy alkyl groups or the groups $R_3$ and $R_5$ together with the two carbon atoms may form the basic structure of a cycloaliphatic ring.

The present invention also relates to the new polyisocyanates obtainable by this process and to their use as starting components for the production of polyurethane resins by the isocyanate polyaddition process.

DETAILED DESCRIPTION OF THE INVENTION

The hydroxyl compounds which are used in the process according to the invention, and which are essential to this process, are preferably compounds represented by the above formula in which $R^1$ and $R^2$ are the same or different and represent hydrogen, $C_2$ to $C_{18}$, in particular $C_2$ to $C_6$, hydroxy alkyl groups, $C_1$ to $C_{18}$, in particular $C_1$ to $C_4$, alkyl groups, or $C_4$ to $C_{15}$, in particular $C_6$ to $C_{10}$, cycloalkyl groups, at least one of the groups $R^1$ and $R^2$ representing hydrogen or a hydroxy alkyl group, $R_3$, $R_4$, $R_5$ and $R_6$ are the same or different and represent hydrogen, $C_1$ to $C_{18}$, in particular $C_1$ or $C_2$, alkyl groups or $C_1$ to $C_{18}$, in particular $C_1$ or $C_2$, hydroxy alkyl groups, or the groups $R_3$ and $R_5$ together with the two carbon atoms form the basic structure of a cycloaliphatic ring having 5 or 6 carbon atoms, and at least two of the groups $R_3$, $R_4$, $R_5$ and $R_6$ represent hydrogen.

Those hydroxyl compounds represented by the above general formula in which $R^1$ and $R^2$ have the meaning already indicated and three of the symbols $R_3$, $R_4$, $R_5$ and $R_6$ represent hydrogen and one of the said symbols represents a methyl or hydroxy methyl group are particularly preferred.

Hydroxyl compounds represented by the above general formula in which at least one of the groups $R^1$ or $R^2$ is a $C_4$ to $C_8$ hydroxy alkyl group interrupted by ether oxygen bridges or a hydroxy-cyclohexyl-cyclohexyl-ether group are also suitable for the process according to the invention but less advantageous. Apart from the above mentioned hydroxyl compounds represented by the general formula indicated above, compounds represented by this formula in which the groups $R^1$ to $R^6$ carry substituents which are inert under the conditions of the process, e.g. alkoxy groups or halogen atoms, are, of course, also suitable for the process according to the invention.

The hydroxyl compounds of the above general formula, which are essential for the invention, can easily be prepared be reacting compounds containing amino groups, as represented by the following formula:

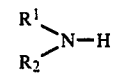

with cyclic carbonates represented by the following formula:

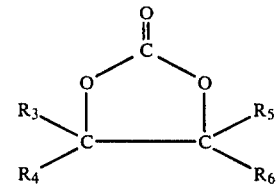

In these last two formulae, $R_1$ to $R_6$ have the meanings already indicated.

The following are examples of suitable compounds containing amino groups: ammonia; methylamine; ethylamine; propylamine; isopropylamine; butylamine; sec.-butylamine; isobutylamine; tertiary butylamine; pentylamine; tertiary pentylamine; hexylamine; 2-ethyl hexylamine; dodecylamine; tetradecylamine; hexadecylamine; octadecylamine; 2-propenylamine; cyclohexylamine; 2(or 3 or 4)-methylcyclohexylamine; aminomethylcyclohexylamine; 3,3,5-trimethylcyclohexylamine; 2-norbornylmethylamine; 2-aminoethanol; 3-amino-1-propanol; 1-amino-2-propanol; 4-amino-2-butanol; 3-amino-1-butanol; 2-amino-1-butanol; 3-amino-3-methyl-1-butanol; 2-amino-2-methyl-1-propanol; 2-amino-2-methyl-1,3-propane diol; 2-amino-2-hydroxymethyl-1,3-propane diol; 5-amino-1-pentanol; 3-amino-2,2,4-trimethyl 1-pentanol; 6-amino-1-hexanol; methyl-hexanolamine (isomeric mixture); trimethyl-1,6-hexanolamine (isomeric mixture); 2,2-dimethyl-3-amino-1-hexanol; 7-amino-1-heptanol; 10-amino-1-decanol; 12-amino-1-dodecanol; 2(3 or 4)-aminocyclohexanol; 2(or 3)-methyl-4-amino-cyclohexanol; 2-(or 6)-methyl-3-amino-cyclohexanol; 5(or 6)-methyl-2-amino-cyclohexanol; 2(3 or 4)-aminomethylcyclohexanol; 2-(3-aminopropyl)-cyclohexanol; 3-aminomethyl-3,3,5-trimethyl-cyclohexanol; 4-(2-aminoethyl)-(2-hydroxyethyl)cyclohexane; 1-hydroxy methyl-3(or 4)-amino-methylcyclohexane; 2-hydroxy methyl-5(or 6)-aminomethylbicyclo-2,2,1-heptane; 1-hydroxy-5(6 or 7)-amino decahydro naphthalene; 2-hydroxy-6(or 7)-amino-decahydro naphthalene; 1-aminomethyl-2-hydroxy-decahydro naphthalene; 4-amino-4'-hydroxy-dicyclohexyl methane; 2-(4-aminocyclohexyl)-2-(4-hydroxy cyclohexyl)propane; 2-methylamino ethanol; N-(2-hydroxyethyl)-cyclohexylamine; 1-cyclohexylamino-2-propanol; bis-(2-hydroxyethyl)-amine and bis-(2-hydroxypropyl)-amine.

Compounds with an ether structure containing amino groups are also suitable, such as 3-methoxy propylamine, 3-ethoxy propylamine; (3-aminopropyl)butyl ether or 4-hydroxy-4'-amino-dicyclohexyl ether or those compounds which can be obtained by, for example, monoaddition of acrylonitrile to glycols followed by reduction, such as

HO—(CH₂)₂—O—(CH₂)₃—NH₂

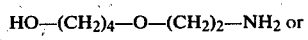

HO—(CH₂)₄—O—(CH₂)₂—NH₂ or

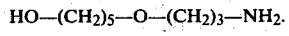

HO—(CH₂)₅—O—(CH₂)₃—NH₂.

The following are examples of suitable cyclic carbonates, 1,3-dioxolan-2-one, 4-methyl-1,3-dioxolan-2-one, 5-methyl-1,3-dioxane-2-one, 5-dimethyl-1,3-dioxane-2-one, 5-ethyl-1,3-dioxan-2-one, 5-diethyl-1,3-dioxan-2-one, 4-hydroxymethyl-1,3-dioxolan-2-one and 2,4-dioxa-bicyclo-4,3,0-nonan-3-one.

Preparation of the hydroxyl compounds used according to the invention is generally carried out at a temperature of from about 20° to 100° C., preferably about 30° to 50° C., by reacting equimolar quantities of the aminocompounds indicated above as examples with the cyclic carbonates given above as examples.

The isocyanates used for the process according to the invention may be any organic polyisocyanates, in particular diisocyanates, having aliphatically and/or cycloaliphatically-bound isocyanate groups. Examples of such isocyanates include ethylene diisocyanate; 1,4-tetramethylene diisocyanate; 2,2,4-(or 2,4,4)-trimethyl-hexamethylene diisocyanate-(1,6); 1,12-dodecane diisocyanate; lysinediisocyanate-(C₁-C₈-alkyl esters); cyclobutane-1,3-diisocyanate; cyclohexane-1,3- and 1,4-diisocyanate and any mixtures of these isomers; hexahydrotolylene-2,4- and -2,6-diisocyanate and any mixtures of these isomers; hexahydrotolylene-2,4- and -2,6-diisocyanate and any mixtures of these isomers; 3,3'-dimethyl-4,4'-diisocyanato dicyclohexyl methane; 4,4'-diisocyanato dicylohexyl methane and xylylene diisocyanate.

Hexamethylene diisocyanate and 1-isocyanato-3,3,5-trimethyl-5-isocyanato methyl-cyclohexane (isophorone diisocyanate) are preferably used.

The process according to the invention is carried out at a temperature of from about 90° to 200° C., preferably about 100° to 180° C. The reactants are put into the process in proportions corresponding to an NCO/OH equivalent ratio of at least about 4:1, preferably from about 6:1 to 25:1.

The process according to the invention may, for example, be carried out as follows:

From 6 to 25 isocyanate equivalents of an aliphatic or cycloaliphatic diisocyanate are introduced into a stirrer vessel under an inert gas atmosphere (nitrogen or argon) and heated to about 100° to 180° C. One hydroxyl equivalent of the hydroxyl compound according to the invention is then introduced into the isocyanate mixture with vigorous stirring. Heating is then continued at about 100° to 180° C. for a period of from 20 minutes to 4 hours, preferably from 1 to 3 hours. A constant isocyanate content is established during this time. The reaction is then completed and excess isocyanate is removed by a known distillation or extraction process (for example using n-hexane or cyclohexane).

The process according to the invention may equally well be carried out in two stages. In that case the starting components are stirred together at room temperature and then heated to a temperature of from about 100° to 180° C. A solvent which is inert towards isocyanates may also be used, e.g. ethyl acetate, butyl acetate, toluene or xylene, but the process according to the invention is preferably carried out without solvent.

The products of the process are viscous, colorless to yellow polyisocyanates which are liquids or solid, hard resins at room temperature. They are completely odorless and dissolve to clear solutions in solvents which are inert towards isocyanate groups, such as hydrocarbons, chlorinated hydrocarbons, esters or ketones.

In the process according to the invention, the hydroxyl groups of the essential hydroxyl compound according to the invention first react with a part of the isocyanate groups of the diisocyanate to form urethane groups. The resulting urethane polyisocyanates which constitute an intermediate stage of the process are obtained at temperatures of between about 50° C. and 100° C. and can be isolated if the temperature is correctly controlled because virtually no allophanate formation occurs at these temperatures. At higher temperatures, above about 100° C., the urethane groups undergo further addition with diisocyanate to form allophanates. If a high temperature, say about 150° C., is employed from the beginning of the reaction so that the urethane alcohol can react with diisocyanate, conversion of the hydroxyl function into urethane groups and formation of allophanate groups take place unselectively and side-by-side.

The method of carrying out the reaction selectively by suitably controlling the reaction temperatures as described above opens up the interesting possibility of synthesizing allophanate polyisocyanates with a predetermined structure containing, for example, both aliphatically and cycloaliphatically bound isocyanate groups. Thus, for example it is possible by maintaining a temperature range of between about 50° and 100° C.

and using an NCO/OH equivalent ratio of 1:1 first to produce a urethane polyisocyanate having either exclusively aliphatically bound or exclusively cycloaliphatically bound isocyanate groups, as desired, and then to carry out the allophanatization reaction at a temperature range of from about 100° to 180° C., in particular about 110° to 150° C., using excess quantities of a cycloaliphatic or aliphatic diisocyanate.

Hydroxyl compounds according to the invention which are particularly suitable for this selective reaction are the corresponding addition products of ammonia with the cyclic carbonates mentioned as examples.

In all the embodiments of the process according to the invention, any excess diisocyanate present after the reaction according to the invention may be removed by distillation, for example in a thin layer evaporator.

The process according to the invention has the following particular advantages:

1. It makes it possible to prepare physiologically substantially harmless allophanate polyisocyanates of low viscosity which are particularly suitable for use in solvent-free or low solvent lacquers;

2. The products obtained by the process according to the invention are light in color and both for this reason, and because the isocyanate groups are aliphatically or cycloaliphatically bound, the products are particularly suitable for the production of light-fast polyurethane lacquers, and 3. Because of the possibility of carrying out the reaction selectively, the process according to the invention can be used for producing specifically defined polyisocyanates whose physical and chemical properties can be adapted to their particular use by suitable choice of the various diisocyanates used as starting materials.

The products of the process according to the invention are valuable starting materials for the production of polyurethane resins by the isocyanate polyaddition process, in particular for the production of one-component or two-component polyurethane lacquers. If the products according to the invention are used in a form in which the isocyanate groups are blocked with known blocking agents, they are also particularly suitable for the production of polyurethane stoving lacquers.

If the products produced by the process according to the invention, which may be in blocked form, are to be used for the production of polyurethane lacquers, the compounds with which they are reacted are preferably the polyhydroxy polyesters, polyhydroxy polyacrylates and optionally low molecular weight, polyhydric alcohols conventionally used for polyurethane lacquers. Suitable reactants of this kind have been described, for example, in German Auslegeschrift No. 2,304,893 and in the texts High Polymers, Vol. XVI, "Polyurethanes, Chemistry and Technology" by Saunders-Frisch, Interscience Publishers, New York, London, Volume I, 1962, pages 32–43 and pages 44–54, and Volume II, 1964, pages 506 and 198–199, and in Kunststoff-Handbuch, Volume VII, Vieweg-Höchtlen, Carl-Hanser Verlag, Munich, 1966, e.g. on pages 45 to 71.

For producing polyurethane lacquers, the polyisocyanates according to the invention, which may be in blocked form, and the reactants mentioned above are generally reacted together in proportions corresponding to about 0.8–3, preferably about 0.9–1.1, hydroxyl, amino, mercapto and/or carboxyl groups to one isocyanate group which may be blocked.

Hardening may be accelerated in known manner by the usual catalysts used in isocyanate chemistry, e.g. tertiary amines such as triethylamine, pyridine, methyl pyridine, benzyl dimethylamine, N,N-dimethylamino cyclohexane, N-methyl piperidine, pentamethyl diethylene triamine, N,N'-endoethylene piperazine, N,N'-dimethyl piperazine and the like, metal salts such as Iron(III)-chloride, zinc chloride, zinc-2-ethyl caproate, tin(II)-2-ethyl caproate, dibutyl tin(IV)-dilaurate, molybdenum glycolate, etc.

When the allophanate polyisocyanates are used in one-component lacquers, the hydroxyl functional reactants used are again mainly those mentioned above.

They are used in proportions corresponding to at least about 1.2, preferably from about 1.5 to 10 isocyanate groups for each hydroxyl group. The reaction gives rise to lacquer binders which contain free isocyanate groups and harden in moist air to hard, glossy, high-quality coatings. The catalysts mentioned above may also be used for one-component lacquers.

When allophanate polyisocyanates are to be used in stoving lacquers, the isocyanate groups are partly or completely blocked in known manner. The polyisocyanate is reacted with a simple blocking agent, preferably at an elevated temperature, e.g. about 40° to 140° C., optionally in the presence of a suitable catalyst such as a tertiary amine or a metal salt such as zinc-2-ethyl caproate, tin(II)-2-ethyl caproate, dibutyl tin (IV)-dilaurate or an alkyl metal phenolate.

The following are examples of suitable blocking agents for the allophanate polyisocyanates of the present invention: Monophenols such as phenol, the cresols, the trimethyl phenols and tertiary butyl phenols; tertiary alcohols such as tertiary butanol, tertiary amyl alcohol and dimethyl phenyl carbinol; compounds which readily form enols, such as ethyl acetoacetate, acetyl acetone and malonic acid derivatives such as malonic acid diesters having from 1 to 8 carbon atoms in the alcohol groups; secondary aromatic amines such as N-methylaniline, N-methyl toluidines, N-phenyl toluidene and N-phenyl xylidene; imides such as succinimide; lactams such as ε-caprolactam and δ-valerolactam; oximes such as butanone oxime and cyclohexanone oxime; mercaptans such as methyl mercaptan, ethyl mercaptan, butyl mercaptan, 2-mercaptobenzo thiazole, α-naphthyl mercaptan and dodecyl mercaptan.

To manufacture the lacquer binders, the allophanate polyisocyanates which may be blocked, the polyfunctional reactants, the catalyst and optionally the usual additives such as pigments, dyes, fillers and levelling agents are mixed thoroughly and homogenized in one of the usual mixing apparatuses such as a sand mill, either with or without solvent or diluent.

The paints and coating compounds produced from the allophanate polyisocyanates of the present invention may be applied to surfaces in a solvent-free, liquid form in solution or from the melt or in solid form by the usual methods such as brush coating, roller application, casting, spraying, the whirl sintering process or the electrostatic powder spray process.

Lacquers containing the polyisocyanates according to the invention give rise to films which adhere surprisingly firmly to metallic surfaces, are exceptionally light-fast, are resistant to discoloration in the heat, are highly abrasion-resistant and, if used in air-drying lacquers, become surface dry exceptionally rapidly even at temperatures around 0° C. They are also distinguished by great hardness, elasticity, chemical resistance, high gloss, excellent weather resistance and pigment absorption capacity.

The following Examples serve to explain the invention. All percentages given are percentages by weight.

EXAMPLES

Example 1

2018 g (12 mol) of hexamethylene diisocyanate are introduced into a three-necked flask under a nitrogen atmosphere and heated to 150° C. 149 g (1 mol) of N-(2-hydroxyethyl)-2-hydroxyethyl carbamate are added dropwise from a dropping funnel over a period of 20 minutes. Stirring is then continued for 2 hours at 150° C. To isolate the polyisocyanate, the reaction mixture is evaporated by thin layer evaporation in a high vacuum (0.2 Torr) at 170° C., i.e. the excess diisocyanate is removed by distillation in the thin layer evaporator and the product of the process is isolated as distillation residue.

Yield: 720 g
Viscosity: 40,000 cP/25° C.
NCO-content: 17.5%

The urethane polyisocyanate formed from one mol of the carbamate and two mols of the diisocyanate would have a molecular weight of 485. If this urethane diisocyanate had been formed exclusively the maximum yield would have been 485 g. The yield of 720 g shows that there must have been allophanate formation which allophanate formation is also confirmed by the IR spectrum which shows typical allophanate edges at 1725 cm$^{-1}$ and 1540 cm$^{-1}$. Analogous observations can be made in the following examples.

Example 2

Employing the method of Example 1, 163 g (1 mol) of N-(2-hydroxyethyl)-2-hydroxy-1(or 2)-methyl ethyl carbamate* are added to 2018 g (12 mol) of hexamethylene diisocyanate at 150° C. over a period of 20 minutes.

(*)prepared from 2-aminoethanol and 4-methyl-1,3-dioxolan-2-one to produce a homologous mixture containing the methyl substituent both in the 1- and in the 2-position.

After two hours stirring, the reaction mixture is cooled and the product is isolated by thin layer evaporation (170° C./0.1 Torr).

Polyisocyanate yield: 680 g
Viscosity: 18,000 cP/25° C.
NCO-content: 17.4%

Example 3

163 g (1 mol) of N-(3-hydroxypropyl)-2-hydroxy ethyl carbamate are added dropwise over a period of about 20 minutes to 2018 g (12 mol) of hexamethylene diisocyanate which has been preheated to 150° C. The reaction is completed after a further 4 hours stirring at 150° C. After thin layer distillation, the polyisocyanate is isolated as distillation residue.

Yield: 700 g
Viscosity: 18,300 cP/25° C.
NCO-content: 21.7%

Example 4

2018 g (12 mol) of hexamethylene diisocyanate are introduced into the reaction vessel and heated to 150° C. 177 g (1 mol) of N-(3-hydroxypropyl)-2-hydroxy-1(or 2)-methyl-ethyl carbamate are added dropwise over a period of about 20 minutes. The reaction is completed after a further 2 hours stirring. The polyisocyanate is isolated as distillation residue by thin layer distillation.

Yield: 600 g
Viscosity: 5000 cP/25° C.
NCO-content: 17.4%

Example 5

177 g (1 mol) of N-(2-hydroxypropyl)-2-hydroxy-1(or 2)-methyl-ethyl carbamate are added to 2018 g (12 mol) of hexamethylene diisocyanate at 150° C. over a period of about 20 minutes. After a further 1 hour of stirring, the polyisocyanate is isolated as distillation residue by thin layer distillation.

Yield: 650 g
Viscosity: 12,000 cP/25° C.
NCO-content: 18.0%

Example 6

1009 g (6 mol) of hexamethylene diisocyanate are introduced into the reaction vessel and heated to 150° C. 95 g (0.5 mol) of N-(1,1'-dimethyl-2-hydroxyethyl)-2-hydroxy-1(or 2)-methyl-ethyl carbamate are added dropwise over a period of about 15 minutes. After a further 30 minutes stirring, the reaction mixture is worked up by thin layer distillation.

Yield: 350 g
Viscosity: 4,200 cP/25° C.
NCO-content: 17.2%

Example 7

2018 g (12 mol) of hexamethylene diisocyanate are heated to 150° C. in a three-necked flask and 105 g (1 mol) of 2-hydroxy ethyl carbamate are added at this temperature over a period of about 20 minutes. After 4 hours stirring, the reaction mixture is worked up by thin layer distillation, polyisocyanate being isolated as distillation residue.

Yield: 660 g
Viscosity: 27,000 cP/25° C.
NCO-content: 17.5%

Example 8

119 g (1 mol) of 2-hydroxy-1(or 2)-methyl-ethyl carbamate are added over a period of about 20 minutes to 2018 g (12 mol) of hexamethylene diisocyanate which has been preheated to 150° C. The reaction is completed after 3 hours stirring and the reaction product is distilled by thin layer evaporation and isolated as distillation residue.

Yield: 909 g
Viscosity: 37,000 cP/25° C.
NCO-content: 18.9%

Example 9

1009 g (6 mol) of hexamethylene diisocyanate and 80 g (0.5 mol) of 2-hydroxy cyclohexyl carbamate are together introduced into a reaction vessel and heated to 150° C. The carbamate melts in the diisocyanate at between 100° and 110° C. and gradually enters into the reaction. After 2 hours further stirring at 150° C., the experiment is stopped and the reaction product isolated by thin layer distillation.

Yield: 386 g
Viscosity: (75% in ethylglycol acetate) 8500 cP/25° C.
NCO-content: (75% solution) 12.1%

Example 10

90 g (0.5 mol) of N-(propyl)-1(or 2)-hydroxymethyl-2-hydroxyethyl-carbamate are added dropwise over a period of 15 minutes to 1009 g (6 mol) of hexamethylene diisocyanate which has been preheated to 150° C. The reaction is completed after 2 hours. The reaction product is then isolated by thin layer evaporation in a high vacuum.

Yield: 343 g
Viscosity: 10,000 cP/25° C.
NCO-content: 18.4%

Example 11

108 g (0.5 mol) of N-(cyclohexyl)-1(or 2)-hydroxymethyl-2-hydroxyethyl-carbamate are added over a period of 10 minutes to 1009 g (6 mol) of hexamethylene diisocyanate which has been preheated to 150° C. After a further 4 hours stirring, the reaction product is isolated by thin layer evaporation and the polyisocyanate obtained as distillation residue is dissolved to form a 75% solution in ethyl glycol acetate.

Yield: (100%): 350 g
Viscosity (solution): 390 cP/25° C.
NCO-content (solution): 13%

Example 12

1009 g (6 mol) of hexamethylene diisocyanate are introduced into a reaction vessel and heated to 150° C. 103 g (0.5 mol) of N-(bis-(2-hydroxyethyl))-2-hydroxy-1-(or 2)-methyl ethyl carbamate are added dropwise over a period of 10 minutes. After 4 hours at 150° C., the reaction is completed and the reaction product is isolated by thin layer evaporation.

Yield: 400 g
Viscosity: 1500 cP/25° C.
NCO-content: 17.5%

Example 13

504 g (3 mol) of hexamethylene diisocyanate are introduced into a reaction vessel and 48 g (0.25 mol) of N-(bis-(2-hydroxyethyl))-2-hydroxyethyl carbamate are added from a dropping funnel over a period of 5 minutes at 150° C. Stirring is then continued for 4 hours at 150° C., the reaction mixture is filtered to remove any cloudiness present, and the product is isolated by thin layer evaporation in a high vacuum.

Yield: 182 g
Viscosity: 20,000 cP/25° C.
NCO-content: 18.1%

Example 14

52 g (0.25 mol) of N-(1,1'-dihydroxymethyl-ethyl)-2-hydroxy-1-(or 2)-methyl-ethyl carbamate and 1009 g (6 mol) of hexamethylene diisocyanate are together heated to 150° C. for 2½ hours. Excess hexamethylene diisocyanate is then removed by thin layer evaporation.

Yield: 233 g
Viscosity: 12,000 cP/25° C.
NCO-content: 17.8%

The preparation of polyisocyanates having both cycloaliphatically bound isocyanate groups and isocyanate groups bound as end groups in linear chains is described in Examples 15 and 16 below.

Example 15

111 g (½ mol) of isophorone diisocyanate are introduced into a reaction vessel and 53 g (½ mol) of 2-hydroxyethyl carbamate are added dropwise at 80° C. The reaction is carried out at 80° C. for about 4 hours, until the theoretical isocyanate content is obtained. 1009 g (6 mol) of hexamethylene diisocyanate are then run into the reaction mixture and the temperature is raised to 150° C. The reaction is completed after three hours and the reaction product is isolated by thin layer evaporation in a high vacuum.

Yield (100%): 315 g
Viscosity (80% in ethylglycol acetate): 5500 cP/25° C.
NCO-content (80% solution): 13.5%

Example 16

120 g (1 mol) of 2-hydroxy-1(or 2)-methyl-ethyl carbamate are added dropwise at 80° C. to 222 g (1 mol) of isophorone diisocyanate. When the required isocyanate content is reached, after 4 hours stirring, 2018 g (12 mol) of hexamethylene diisocyanate are added to the reaction mixture which is then heated to 150° C. for 4 hours. The excess isocyanate is then removed by thin layer evaporation to isolate the reaction product which is then dissolved to form an 80% solution in ethylglycol acetate.

Yield: 630 g (100%)
Viscosity: 6100 cP/25° C. (80%)
NCO-content: 12.8% (80%)

Example 17

The stability of the polyisocyanates prepared is tested in some Examples by several weeks tempering at 50° C. followed by determination of the monomeric isocyanate content of the samples by gas chromatographic analysis.

| Polyisocyanate from Example | Monomeric diisocyanate content (%) | | | | |
|---|---|---|---|---|---|
| | O-value | after 4 wks | after 8 wks | after 12 wks | after 16 wks |
| 2 | 0.72 | 0.74 | 0.74 | 0.7 | 0.73 |
| 4 | 0.54 | 0.31 | 0.23 | 0.45 | 0.48 |
| 5 | 0.28 | 0.26 | 0.29 | 0.27 | — |
| 6 | 0.18 | 0.21 | 0.20 | 0.24 | — |
| 8 | 0.79 | 0.72 | 0.75 | — | — |
| 16 | 0.64 | 0.63 | 0.65 | — | — |

This experiment demonstrates very clearly that the products obtained by the process according to the invention are virtually resistant to decomposition into the original monomers. From a physiological point of view, this is a particularly important criterion for deciding whether the products are suitable for use as lacquer polyisocyanates.

Although the invention has been described in detail for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of allophanate polyisocyanates having at least three isocyanate groups by the reaction of hydroxyl compounds with excess quantities of organic polyisocyanates which are free from allophanate groups, characterized in that the hydroxyl compounds used contain compounds represented by the following formula

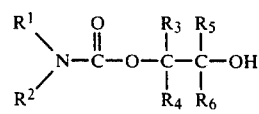

wherein
- $R^1$ and $R^2$ are identical or different and represent hydrogen or hydroxyalkyl, alkyl or cycloalkyl groups wherein at least one of the groups $R^1$ and $R^2$ must be hydrogen or a hydroxy alkyl group, and
- $R_3$, $R_4$, $R_5$ and $R_6$ are identical or different and represent hydrogen or alkyl or hydroxy alkyl groups or the groups $R_3$ and $R_5$ together with the two carbon atoms may form the basic structure of a cycloaliphatic ring.

2. The process of claim 1 wherein
- $R^1$ and $R^2$ are the same or different and represent hydrogen, $C_2$ to $C_{18}$ hydroxy alkyl groups, $C_1$ to $C_{18}$ alkyl groups or $C_4$ to $C_{15}$ cycloalkyl groups, at least one of the groups $R^1$ or $R^2$ representing hydrogen or a $C_2$ to $C_{18}$ hydroxy alkyl group, and
- $R_3$, $R_4$, $R_5$ and $R_6$, are the same or different and represent hydrogen, $C_1$ to $C_{18}$ alkyl groups, $C_1$ to $C_{18}$ hydroxy alkyl groups or the groups $R_3$ and $R_5$ together with the two attached carbon atoms form the basic structure of a cycloaliphatic ring having 5 to 6 carbon atoms, and at least two of the groups $R_3$, $R_4$, $R_5$ and $R_6$ represent hydrogen.

3. The process of claim 1 wherein the NCO/OH equivalent ratio of organic polyisocyanates to hydroxyl compounds is at least about 4:1.

4. The process of claim 3 wherein NCO/OH equivalent ratio is from about 6:1 to 25:1.

5. Allophanate group-containing polyisocyanates produced by the process of claim 1.

6. In a process for the production of polyurethane resins by the isocyanate polyaddition process, the improvement comprising reacting polyhydroxy compounds with the allophanate-polyisocyanates produced by the process of claim 1.

7. The process of claim 6 wherein the allophanatepolyisocyanates are present in blocked form.

8. The process of claim 1 wherein the allophanate polyisocyanates are prepared in the absence of catalysts.

9. The process of claim 1 wherein a constant isocyanate content is established after heating the hydroxyl compounds and the organic polyisocyanate for from 20 minutes to 4 hours.

* * * * *